US00PP28862P3

(12) United States Plant Patent
Stemkens

(10) Patent No.: US PP28,862 P3
(45) Date of Patent: Jan. 9, 2018

(54) *AUBRIETA* PLANT NAMED 'ABRZ0005'

(50) Latin Name: *Aubrieta hybrida*
Varietal Denomination: ABRZ0005

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 59 days.

(21) Appl. No.: 14/999,551

(22) Filed: May 23, 2016

(65) Prior Publication Data

US 2017/0135263 P1 May 11, 2017

Related U.S. Application Data

(60) Provisional application No. 62/252,740, filed on Nov. 9, 2015.

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Keith O Robinson
(74) *Attorney, Agent, or Firm* — Dale Skalla

(57) ABSTRACT

A new *Aubrieta* plant named 'ABRZ0005' particularly distinguished by its purple flowers with a white eye, a compact and mounding habit with strong vigor, and a good winter hardiness.

1 Drawing Sheet

Latin name of the genus and species of the plant claimed: *Aubrieta hybrida.*

Varietal denomination: 'ABRZ0005'.

BACKGROUND OF THE NEW PLANT

The present invention comprises a new *Aubrieta*, botanically known as *Aubrieta hybrida* and hereinafter referred to by the variety name 'ABRZ0005'.

'ABRZ0005' is a product of a planned breeding program. The new cultivar 'ABRZ0005' has purple flowers with a white eye, a compact and mounding habit with strong vigor, and is very winter hardy.

'ABRZ0005' originates from a hybridization in a controlled breeding program in a greenhouse in Enkhuizen, The Netherlands. The female parent was an unpatented, proprietary plant identified as 'J3025-5' with violet flowers and more branching compared to 'ABRZ0005'.

The male parent of 'ABRZ0005' was an unpatented, proprietary plant identified as 'G1463-51' with a red flower color with an eye, less branching and later flowering compared to 'ABRZ0005'. The resultant seed was sown in August 2008 in a greenhouse in Enkhuizen, The Netherlands.

'ABRZ0005' was selected as one flowering plant within the progeny of the stated cross in March 2009 in a greenhouse in Enkhuizen, The Netherlands.

The first act of asexual reproduction of 'ABRZ0005' was accomplished when vegetative cuttings were propagated from the initial selection in June 2009 in a greenhouse in Enkhuizen, The Netherlands.

BRIEF SUMMARY OF INVENTION

Horticultural examination of plants grown from cuttings of the plant initiated in August 2009 in Enkhuizen, The Netherlands, and continuing thereafter, has demonstrated that the combination of characteristics as herein disclosed for 'ABRZ0005' are firmly fixed and are retained through successive generations of asexual reproduction.

'ABRZ0005' has not been observed under all possible environmental conditions. The phenotype may vary significantly with variations in environment such as temperature, light intensity, and day length.

A Plant Breeder's Right for this cultivar was applied for in the European Union on May 27, 2015 and assigned application no. 2015/1073. 'ABRZ0005' has not been made publicly available more than one year prior to the filing of this application.

The following traits have been repeatedly observed and are determined to be basic characteristics of the new variety. The combination of these characteristics distinguishes this *Aubrieta* as a new and distinct variety.

BRIEF DESCRIPTION OF THE PHOTOGRAPH

The accompanying photographic drawing shows typical flower and foliage characteristics of 'ABRZ0005' with colors being as true as possible with an illustration of this type. The photographic drawing shows in FIG. 1 a close-up of the flowers.

DETAILED BOTANICAL DESCRIPTION

The plant descriptions and measurements were taken in Enkhuizen, The Netherlands under natural light in March 2015. These plants were approximately 22 weeks old and were growing in 13 cm pots, in shade-house trials.

The plants used for the photographs were about 22 weeks old, grown in Enkhuizen, The Netherlands and taken in March 2015.

Color Chart used: Royal Horticultural Society Colour Chart (R.H.S.) 2001

TABLE 1

DIFFERENCES BETWEEN THE NEW VARIETY 'ABRZ0005' AND A SIMILAR VARIETY

| | 'ABRZ0005' | 'Axcent Violet with Eye' |
|---|---|---|
| Plant shape: | Vigorous | Compact |
| Earliness: | 2 weeks earlier | Later |
| Flower color: | More purple | More violet |

Plant:

*Form, growth and habit.*—Mounding, spreading.
*Plant height.*—7 cm.
*Plant height (inflorescence included).*—9 cm.
*Plant width.*—22 cm.

Roots:

*Number of days to initiate roots.*—About 6 days at 18 degrees C.
*Number of days to produce a rooted cutting.*—2.5 weeks at 18 degrees C.
*Type.*—Fine, fibrous, free branching.
*Color.*—RHS N155B but whiter.

Foliage:

*Arrangement.*—Alternate.
*Immature, leaf color, upper surface.*—RHS 147A.
*Immature, leaf color, lower surface.*—RHS 147B.
*Mature, leaf color, upper surface.*—RHS 146B.
*Mature, leaf color, lower surface.*—RHS 146C.
*Length.*—2.5 cm.
*Width.*—1.8 cm.
*Shape.*—Oblanceolate.
*Base shape.*—Attenuate.
*Apex shape.*—Obtuse.
*Margin.*—Slightly dentate.
*Texture.*—Pilose.
*Color of veins, upper surface.*—RHS 143C.
*Color of veins, lower surface.*—RHS 146C.
*Pattern of veining.*—Pinnate.
*Petioles color.*—RHS 146C.
*Petioles length.*—1-1.2 cm.
*Diameter of petiole.*—0.5 cm.
*Texture.*—Glabrous.

Stem:

*Color of stem.*—RHS 144C to RHS 144D.
*Length of stem.*—5 cm.
*Diameter.*—0.2-0.4 cm.
*Length of internodes.*—0.5 cm.
*Texture.*—Pilose.
*Color of peduncle.*—RHS 144B with brownish pigments RHS 165A.
*Length of peduncle.*—1-1.5 cm.
*Peduncle diameter.*—0.3 cm.
*Texture.*—Pilose.
*Color of pedicel.*—RHS 144B with RHS 165A.
*Length of pedicel.*—1.6 cm.
*Diameter of pedicel.*—0.15 cm.
*Texture.*—Pubescent.

Inflorescence:

*Type.*—Single, cruciform, composed of 4 petals, flowers held above the plant.
*Number of flowers per inflorescence.*—10-15.
*Quantity of inflorescences per plant.*—About 35.
*Lastingness individual blooms on the plant.*—15 days.
*Fragrance.*—None.

Bud (just before opening/showing color):

*Color.*—is the color of the sepals: RHS 189A to RHS187A.
*Length.*—0.8 cm.
*Width.*—0.5 cm.
*Shape.*—Oblong.

Corolla:

*Immature inflorescence.*—Diameter: 1.2 cm. Color petals, upper surface: Very deep RHS N81A. Color petals, lower surface: RHS N81A edges to RHS N87A near the center.
*Mature inflorescence.*—Form: Petals folding backwards on the calyx. Flower diameter: 1.7-2 cm. Depth of flower: 1.7 cm.
*Number of petals.*—4.
*Color upper petals, upper surface.*—RHS N81A turning RHS 1B at the base (eye).
*Color upper petals, lower surface.*—RHS N81B turning RHS 151D at the base.
*Length of petals.*—2.2 cm.
*Width of petals.*—1.5 cm.
*Petal shape.*—Spathulate.
*Apex shape.*—Rounded.
*Margin.*—Entire.
*Corolla texture, inside.*—Glabrous, papillose.
*Corolla texture, outside.*—Glabrous, papillose.
*Corolla tube color inside.*—RHS 151D.
*Corolla tub, color outside.*—RHS 151D.
*Duration of flowering.*—Continuous flowering throughout the Spring until end of May.

Calyx:

*Number of sepals.*—4.
*Color of sepals.*—RHS 144B at the top turning to RHS 187A at the base.
*Length of sepals.*—0.9 cm.
*Width of sepals.*—0.2-0.4 cm.
*Sepal shape.*—2 types: 2 are oblanceolate situated on the opposite of each other, and 2 are oblong, also on the opposite of each other. The particularity is that the 2 oblong sepals are swollen at the base on mature flowers.
*Apex shape.*—
*Oblanceolate shaped sepals.*—Obtuse.
*Oblong shaped sepals.*—Acute.
*Margins.*—Entire.
*Texture, inner/upper surface.*—Smooth.
*Texture, outer/lower surface.*—Stellate hairs.
*Base.*—Fused.

Reproductive organs:

*Gynoecium.*—Pistil quantity: 1. Length: 1 cm. Style color: RHS 144C. Style length: 0.5 cm. Stigma color: RHS N144A. Stigma shape: Disc shaped. Ovary color: RHS 143C. Ovary size: 0.5 cm.
*Androecium.*—Number of stamens: 6. Length of stamens: 1 cm. Anther color: RHS 150C. Anther length: 0.2 cm. Anther shape: Ovate. Length filaments: 0.5-0.9 cm. Color of filaments: RHS 145C. Pollen amount: Moderate. Color of pollen: RHS 1A.
*Fertility/seed set.*—Neither seed nor fruit production has been observed.

*Disease/pest resistance.*—Resistance to pathogens and pests common to *Aubrieta* has not been observed.

*Drought tolerance and cold tolerance.*—Hardy perennial. Tolerates high temperature to at least 30 degrees C. Tolerates low temperatures to degrees minus 22 C. No specific drought tolerance has not been observed.

What is claimed is:

1. A new and distinct variety of *Aubrieta* plant named 'ABRZ0005' substantially as illustrated and described herein.

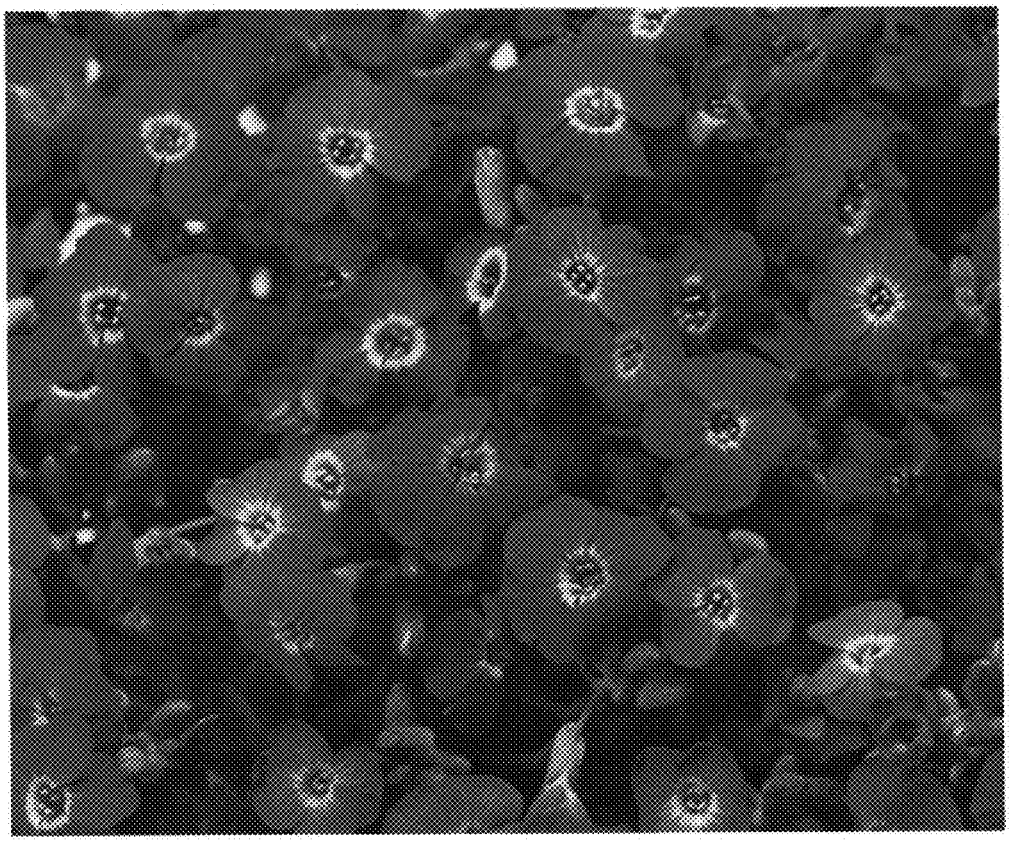

* * * * *